United States Patent [19]

Sarnoff et al.

[11] Patent Number: 4,839,170

[45] Date of Patent: * Jun. 13, 1989

[54] PROTEIN ABSORPTION ENHANCING AGENTS

[75] Inventors: Stanley Sarnoff, Bethesda, Md.; Burton E. Sobel, Webster Groves, Mo.

[73] Assignee: Survival Technology, Inc., Bethesda, Md.

[ * ] Notice: The portion of the term of this patent subsequent to Sep. 20, 2005 has been disclaimed.

[21] Appl. No.: 54,898

[22] Filed: May 28, 1987

Related U.S. Application Data

[63] Continuation-in-part of Ser. No. 782,441, Oct. 1, 1985, Pat. No. 4,772,585.

[51] Int. Cl.$^4$ ............................................. A61K 37/547
[52] U.S. Cl. ..................... 424/94.64; 424/94.63; 424/659; 514/2; 514/12
[58] Field of Search .......................... 424/94.63, 94.64; 514/2, 12

[56] References Cited

U.S. PATENT DOCUMENTS

| | | |
|---|---|---|
| 4,656,034 | 4/1987 | Sarnoff . |
| 4,658,830 | 4/1987 | Sarnoff . |
| 4,661,469 | 4/1987 | Sarnoff . |
| 4,772,585 | 9/1988 | Sarnoff et al. .......................... 514/2 |

OTHER PUBLICATIONS

Sobel et al., Proceeding with Proc. and Natl. Acad. Sci. USA, vol. 82, pp. 4258–4262, Jun. 1985.
Hills et al., Abstract of the 58th Scientific Session Circulation 1984, Oct.; 72(4):III-69.
Fox et al., J.A.C.C., vol. 7, No. 2, Feb. 1986, p. 52A.

*Primary Examiner*—Sam Rosen
*Attorney, Agent, or Firm*—Cushman, Darby & Cushman

[57] ABSTRACT

A package containing (1) t-PA, (2) methylamine or a non-toxic salt thereof and (3) hydroxylamine or a non-toxic salt thereof, the amount of hydroxylamine or non-toxic salt thereof being sufficient to increase the absorption in the blood of the t-PA when it is administered non-intravascularly to a mammal and the amount of methylamine or non-toxic salt thereof being sufficient to reduce the amount of hydroxylamine or non-toxic salt thereof required to obtain the increased absorption of t-PA and a method for intramuscularly administering the same.

16 Claims, No Drawings

PROTEIN ABSORPTION ENHANCING AGENTS

This application is a continuation-in-part of application Ser. No. 782,441 filed Oct. 1, 1985, now U.S. Pat. No. 4,722,585.

RELATED PATENTS AND APPLICATIONS

Sarnoff U.S. Pat. No. 4,658,830 discloses the use of hydroxylamine and its salts to enhance the absorption of a clot selective coronary thrombolytic agent, especially t-PA (tissue-type plasminogen activator), into the blood stream, especially upon intramuscular absorption. This disclosure is expanded in subsequent Sarnoff U.S. Pat. No. 4,661,469, Sarnoff U.S. application Ser. Nos. 716,705, filed Mar. 27, 1985, and Sarnoff 782,441, filed Oct. 1, 1985. Sarnoff U.S. application Ser. No. 782,441 further discloses as the absorption enhancing agent for t-PA lower alkylamines, di lower alkylamines and their non-toxic salts.

Sarnoff U.S. Pat. No. 4,656,034 discloses a medicament (and its intramuscular injection) including a clot selective coronary thrombolytic agent, specifically t-PA, an absorption enhancing agent, specifically hydroxylamine or a non-toxic salt thereof, and a reperfusion damage preventing agent, specifically superoxide dismutase. The entire disclosure of these five Sarnoff patents and applications is hereby incorporated by reference and relied upon. Sarnoff U.S. application Ser. No. 19,564, filed Feb. 27, 1987, is a division of U.S. application Ser. No. 782,441.

Thrombolysis induced by intravenous administration of activators of the fibrinolytic system early after the onset of ischemia aborts myocardial infarction, improves ventricular performance, and prolongs life. Its efficacy depends on the rapidity of implementation early after the onset of ischemia. Immediate intramuscular administration of lifesaving medication, sometimes with the use of autoinjectors, has proven feasible for emergency treatment of severe allergic reactions and potentially lethal arrhythmias.

It has previously been found that intramuscular administration of tissue-type plasminogen activator (t-PA) for coronary thrombolysis also is feasible, see the above mentioned Sarnoff patents and patent applications as well as Sobel et al, "Coronary thrombolysis with facilitated absorption of intramuscularly injected tissue-type plasminogen activator," Proc. Natl. Acad. Sci. USA, Vol. 82, page 4258 (1985) as well as ox et al, J. Amer. College of Cardiology, Vol. 7, No. 2, February 1986, page 52A which discloses methylamine HCl as an absorption enhancing agent for t-PA and Fields et al., Circulation Oct. 1985 III 69 which shows enhanced absorption of proteins with hydroxylamine.

Absorption of t-PA in rabbits was found to be enhanced by the use of hydroxylamine and its non-toxic salts, especially hydroxylamine hydrochloride and preferably coupled with local electrical stimulation at the injection site. Under these conditions, early peak blood levels were attained within 5 minutes. However, in the high concentrations that were required, hydroxylamine and its salts could elicit methemoglobinemia, hypotension, tachycardia, or local injury.

As stated above, Sarnoff U.S. application Ser. No. 782,441 discloses alkyl and dialkylamines and their non-toxic salts, preferably methylamine hydrochloride, as absorption enhancers for t-PA. However, these absorption enhancers have been found to be not as effective as hydroxylamine and its salts.

It has now been found that by the use of a combination of hydroxylamine or a non-toxic salt thereof and methylamine or a non-toxic salt thereof there can be obtained rapid and prolonged enhancement of the absorption of t-PA administered non-intravascularly, e.g., intramuscularly, even without the use of electrical stimulation.

It has further been found that by using methylamine or a non-toxic salt thereof together with ydroxylamine or a non-toxic salt thereof the amount of hydroxylamine or non-toxic salt thereof to produce enhanced absorption of t-PA can be reduced and thus the side effects of hydroxylamine are reduced or eliminated. At the same time the absorption of t-PA is enhanced to a greater extent than could be expected simply from using the methylamine or its salt, i.e., the effect is not simply additive.

Examples of non-toxic salts of hydroxylamine and methylamine are the salts of hydrochloric acid, hydrobromic acid, hydriodic acid, phosphoric acid, sulfuric acid, nitric acid, acetic acid, propionic acid and succinic acid. Preferably there are employed hydroxylamine hydrochloride and methylamine hydrochloride.

The hydroxylamine or non-toxic salt thereof and the methylamine or non-toxic salt thereof are normally administered as aqueous solutions injected intramuscularly. They can be administered from a single vial as a mixed dosage or from separate vials, in which case they are preferably administered substantially simultaneously. Likewise they can be administered as a single dosage from the same vial as the t-PA or can be administered separately from the t-PA, preferably substantially simultaneously.

Preferably the absorption enhancing agent combination (i.e., hydroxylamine or salt thereof and methylamine or salt thereof) is mixed with the t-PA to form a single mixed dosage which is then injected intramuscularly (i.m.), e.g., as described in Sarnoff U.S. Pat. No. 4,658,830.

The hydroxylamine or salt thereof is preferably administered at a concentration of 0.079 molar and the methylamine or salt thereof is preferably administered at a concentration of 0.63 molar. The hydroxylamine or salt thereof can be administered at a dosage of 0.02 molar to 0.79 molar, but is desirably administered at a dosage at which side effects of the hydroxylamine are kept at a minimum, e.g., below 0.5 molar. The methylamine or salt thereof can be administered for example at a concentration of 0.02 molar to 6.3 molar, usually at a concentration of at least 0.15 molar.

Stated another way the hydroxylamine or non-toxic salt thereof is administered in an amount sufficient to increase the absorption of the t-PA introduced non-intravascularly (e.g., intramuscularly) and the methylamine or non-toxic salt thereof is administered in an amount sufficient to reduce the amount of hydroxylamine or non-toxic salt thereof required to impart such increased absorption of t-PA.

In addition as pointed out supra the combination of hydroxylamine or non-toxic salt thereof and the methylamine or non-toxic salt thereof prolongs the elevation of t-PA in the blood.

In the study leading to the present invention hydroxylamine, methylamine and other amines as well as vasodilators, and other agents alone and in combination with low concentrations of hydroxylamine were evaluated in 250 rabbits and 13 dogs to determine their effects on enhancement of absorption of human t-PA given intramuscularly, hemodynamics, and possible confounding effects of enhancers on detectable human t-PA antigen. The combination of agents, methylamine hydrochloride with low and physiologically well-tolerated concentrations of hydroxylamine hydrochloride, was found to promote rapid absorption of t-PA with fibrinolytic and persistent coronary thrombolytic activity attained within 5 minutes after intramuscular injection and maintained for at least 6 hours in dogs without induction of extensive myonecrosis at the site of injection, methemoglobinemia, tachycardia, or hypotension. An additional 31 rabbits and six dogs were studied with injections of media with or without enhancer but without t-PA. After the most favorable conditions had been defined in experiments involving exposure of skeletal muscle at the injection site, intramuscular injections were performed percutaneously without local electrical stimulation, as opposed to directly into exposed muscle with local electrical stimulation.

The results indicate that sustained, therapeutic blood levels of t-PA can be obtained promptly after intramuscular injection without local electrical stimulation and under conditions devoid of deleterious local or systemic side effects and that injections in large laboratory animals induce sustained coronary thrombolytic effects that persist for as long as 6 hours.

The results also indicate that the combination of hydroxylamine or non-toxic salt thereof and methylamine or non-toxic salt thereof also would be useful in enhancing the absorption and prolonged effect of t-PA when it is administered to humans.

MATERIALS AND METHODS

Materials. t-PA in concentrations of 0.5 to 50 mg/ml produced by recombinant DNA technology (rt-PA) was provided by Genentech,Inc., South San Francisco (lots BH004DAX, H9017, and 4869-42). Intramuscular or intravenous administration of excipient alone had no effect on functionally or immunoradiometrically detectable plasma t-PA in rabbits or dogs (n=31 rabbits and six dogs). Intramuscular administration of t-PA in excipient alone yielded virtually no elevation of plasma t-PA within the first 30 minutes in either species. Several potential enhancers of absorption selected because of their known interaction with protease inhibitors or their known rapid absorption were evaluated alone or in combination in concentrations of 0.015M to 1.20M, including diethanolamine, diethylamine, dimethylamine, ethanolamine, ethylamine, histamine, hydroxylamine, methoxyamine, and methylamine. Adenosine and hydralazine were evaluated also because of their potential value as vasodilators augmenting local blood flow and hence absorption of t-PA. Hypertonic saline (0.63M) and hypertonic saline with methylamine were evaluated as well. Hyaluronidase (Sigma, type IVS, 1000 U/mg) was included in the injection medium in some experiments (1 mg/ml) because of its potential utility for facilitating diffusion and absorption. None of the agents affected either immunologically detectable t-PA or functional activity of t-PA despite incubations in vitro with t-PA in plasma or phosphate-buffered saline, pH 7.4 at 37° C. for 1 hour before injection.

Experimental animals. To characterize effects of enhancers on absorption of t-PA in small animal species under the diverse conditions that required evaluation, experiments were performed first in 250 nonfasted, male, New Zealand White rabbits weighing 1.9 to 2.5 kg. Rabbits were selected rather than larger animals because the total amount of t-PA that was available was limited. Some experiments employed direct injection into exposed muscle with or without local electrical stimulation as previously described in the aforementioned Sobel article. Others (n=21) were performed with percutaneous injections. These experiments employed larger concentrations and amounts of t-PA, percutaneous injection, and no electrical stimulation. For the short-term studies in rabbits, animals were anesthetized with 10 mg/kg sodium pentothal and 50 mg/kg $\alpha$-chloralose and instrumented for monitoring of arterial blood pressure via the carotid artery and acquisition of serial blood samples via the jugular vein. In most experiments skin and subcutaneous tissues overlying the sartorius muscles bilaterally were incised, the muscle was exposed, t-PA or excipient alone was injected directly into the exposed muscle, and serial blood samples were acquired sequentially throughout a 30 minute interval via the indwelling jugular venous catheter. In some animals, skeletal muscle blood flow was augmented at the injection site by electrical stimulation of the muscle with 2.0 msec, 9 to 14 V pulses at a rate of 5/sec for 30 minutes as previously described.

In 21 rabbits and in each of 13 dogs studied subsequently, injections were made percutaneously without exposure of the muscle and without electrical stimulation so that the factors favoring absorption that had been defined could be tested under conditions simulating those applicable clinically. For these experiments, concentrations of t-PA in the injection medium were adjusted within the range of 5 mg/ml (rabbits) and 10 m//kg (dogs) with two injections of 1 or 2 ml, respectively.

For studies in dogs, animals weighing approximately 20 kg were anesthetized with 12.5 mg/kg thiopentothal plus 60 mg/kg $\alpha$-chloralose after analgesia with 1 mg/kg morphine sulfate subcutaneously, ventilated with room air with a Harvard respirator via an endotracheal tube, and monitored hemodynamically. Injections of 2 ml aliquots of t-PA or excipient alone were administered intramuscularly into the sartorius muscle manually and percutaneously via syringe through a 21-gauge stainless-steel needle. For studies of coronary thrombolysis, coronary thrombosis was first induced with a thrombogenic copper coil and documented angiographically, as was coronary thrombolysis elicited with t-PA.

To assess the short-term histologic effects of intramuscular injection of excipient with t-PA, injection sites in rabbits and dogs were excised immediately after the final blood sample had been collected and compared with those of the contralateral sartorius muscle into which excipient without t-PA had been injected simultaneously and in equal volume. Tissues were fixed immediately in sodium phosphate-buffered 10% formalin and processed conventionally for light microscopy.

For morphologic studies of longer-term local effects of injections in rabbits, injection sites were marked on the epimysial surface with lissamine green, skin incisions were closed, and the animals were allowed to recover after anesthesia and administration of excipient with or without enhancer, t-PA, or both. Control and test tissue specimens (i.e., 1 cm thick blocks with approximately 4 $cm^2$ cross-sectional area injected with excipient alone and contralateral area injected with excipient alone and contralateral muscle injected with excipient plus enhancer with or without t-PA) were obtained at necropsy, 48 to 96 hours after intramuscular injection, fixed, and prepared as serial 5 μm sections for microscopy.

For studies of effects of enhancers on permeation of radiolabeled tracers, male Sprague-Dawley rats weighing 200 to 450 g were used.

Assay of plasma samples. Immunoradiometrically detectable human t-PA antigen was measured in serial blood samples collected via an indwelling jugular venous catheter in citrate Vacutainer tubes at 0° to 4° C with a final concentration of citrate of 10 mM. Plasma was separated at 4° C. by centrifugation for 10 minutes at 1600 g and stored at -20° C until assayed. t-PA antigen in rabbits was assayed with a two-site immunoradiometric assay (IRMA) procedure as previously described after binding of t-PA to anti-t-PA immunoglobulin G absorbed to wells in a microtiter plate and subsequent binding of I-anti-t-PA to bound t-PA. After removal of excess I-anti-t-PA, the amount of bound I-t-PA was determined by gamma scintillation spectrometry. Anti-t-PA antiserum and purified human melanoma t-PA used as reference standards were provided by Prof. Desire Collen. For convenience, human t-PA antigen in dogs was assayed with a commercially available enzyme-linked immunosorbent assay (ELISA) procedure (American Diagnostica) standardized with the IRMA procedure. Because endogenous t-PA in rabbits or in dogs does not cross-react with human t-PA in the ELISA assay used, it did not influence results.

t-PA functional activity was assayed with fibrin plates and by a modified, microtiter amidolytic chromogenic procedure. Zones of fibrinolysis on plates were measured by planimetry. Plates prepared with human fibrinogen (KabiVitrum), thrombin (Sigma), and $CaCl_2$ (0.05M) were exposed to serial dilutions of euglobulin fraction samples prepared by dilution of citrated plasma (1:20) with distilled water, adjustment of pH to 5.8 for dogs and 6.2 for rabbits with acetic acid, centrifugation, and solubilization of precipitates in imidazole-buffered saline (pH 7.4) containing 0.8% BSA. They were incubated at 37° C. for 18 hours. Quantitative analyses of plasma t-PA functional activity were performed with a modified microtiter amidolytic procedure. Both procedures were standardized with respect to the International Reference Preparation for t-PA (IRP-t-PA).

Effects of intramuscularly administered t-PA on fibrinolytic activity in vivo were monitored over 6 hours in dogs by sequential analyses of fibrinogen, plasminogen, and α-antiplasmin in plasma.

Assessment of changes in vascular permeability. For studies of effects of the enhancers of absorption on an index of the permeability of the microvasculature that was entirely independent of t-PA, vascular permeability was characterized with intravascular radiolabeled tracers. Two small animal species (rabbits and rats) were used to conserve radiolabeled material. The extent to which the enhancers of absorption of t-PA affected vascular permeability of the site of intramuscular injection of the enhancers was reflected by egress of intravascular tracers into the extracellular space. Cr-labeled erythrocytes (Cr-RBC) and Co-labeled EDTA were used as markers of the intravascular and extracellular spaces, respectively. Permeability at the intramuscular injection site of enhancers to intravascular I-labeled BSA (I-BSA) was determined by measuring the tissue-to-blood isotope ratio (TBIR) of I/Cr (TBIR I/Cr). In an analogous manner, the TBIR of Co/Cr (TBIR-Co/Cr) was used to estimate the size of the extravascular space potentially available to I-BSA in tissue. Free I was excluded from the injectate by Sephadex gel filtration, and radioactivity in plasma and tissue fractions and homogenates was shown to be more than 99% protein bound, as reflected by precipitation with 5% trichloroacetic acid.

In the initial experiments of this type, male Sprague-Dawley rats weighing 250 to 400 g were anesthetized with sodium pentobarbitol (40 mg/kg). The left femoral vein and right carotid artery were exposed and cannulated. Cr-RBCs (150μCi in 0.6 to 0.8 ml of a buffer suspension with hematocrit of 40%) were injected into the femoral vein 5 minutes before intramuscular injection of excipient with or without enhancer. In some rats, colloidal carbon (1 ml of a 2% suspension) was injected via the femoral vein for microscopic localization of alterations in endothelial junctions potentially produced by the intramuscular injection of excipient with or without enhancer. I-BSA (13μCi) and Co-EDTA (10μCi) (30 to 50μl of each) were injected intravenously, and immediately thereafter 0.1 ml of excipient with or without absorption enhancers was injected intramuscularly into exposed sartorius muscles bilaterally. Approximately 6 minutes after the intramuscular injection, 2 ml of blood was withdrawn from the carotid arterial cannula into a heparinized syringe for quantification of blood levels of the three radiolabeled tracers. One minute later the heart was removed to arrest the circulation, and both injection sites were excised. Radioactivity in blood and skeletal muscle was quantified with a three-channel gamma scintillation spectrometer with automated correction for background and spillover. In animals given colloidal carbon, excised injection sites were fixed in 10% buffered formalin. After quantification of radioactivity with gamma scintillation spectrometry, tissue was processed for light microscopy to permit identification of endothelial junction delineated by deposition of carbon particles in vessel walls.

Additional experiments were performed in male New Zealand White rabbits anesthetized with 150mg/kg α-chloralose and instrumented similarly. Cr-RBCs (600 μCi in 4 ml of a buffered suspension with hematocrit of 40%) and I-BSA (39 μCi) were injected via the jugular venous catheter 15 and 10 minutes before intramuscular injections of t-PA excipient. Subsequently, 0.1 ml of t-PA excipient was injected intramuscularly into one exposed sartorius muscle and 0.1 ml of excipient with absorption enhancer into the contralateral muscle. Fluorescein, 0.01%, was included in the injection medium to facilitate later identification of the injection site. At selected intervals after intramuscular injections, a sample of blood was withdrawn from the carotid artery, the heart was arrested by bolus injection of saturated potassium chloride, both injection sites were delineated immediately with the use of ultraviolet light and excised, and radioactivity in blood and tissue was quantified by gamma scintillation spectrometry.

Physiologic effects of enhancers of absorption of t-PA injected intramuscularly. Effects of the agents tested for enhancement of absorption on heart rate, arterial pressure, and respiratory rate were evaluated in rabbits. Serial determinations of arterial blood gases and pH as well as hemoglobin and methemoglobin were performed. Hydroxylamine elicited massive methemoglobinemia, hypoxemia, transient tachycardia, and hypotension in the high concentrations required to maximize absorption in injection volumes needed for solubilizing large amounts of t-PA. However, on the basis of observations in rabbits subjected to local electrical stimulation, 0.63M methylamine hydrochloride alone and 0.63M methylamine hydrochloride plus 0.079M hydroxylamine hydrochloride were found to be particularly promising enhancers of absorption of t-PA.

Conditions used in the longer-term experiments performed subsequently were selected on the basis on information acquired from studies of several groups of rabbits undertaken first to define the effects of absorption of t-PA of volume of injection medium per se (0.06 to 4.0 ml, n=13); of pH, total t-PA dose, and concentration of a give enhancer of absorption with injection volume held constant (four 1 ml injections per rabbit) and electrical stimulation used (n=27); and of electrical field stimulation at the injection site (n=22). Judging from the results of these short-term experiments and from histologic findings methylamine hydrochloride (0.63M) alone or in combination with low concentrations of hydroxylamine hydrochloride (0.079M) was selected for further evaluation in intact rabbits and dogs to enhance intramuscular absorption of t-PA injected percutaneously.

Statistical analysis. Group data are expressed as means ±SE (standard error). Differences between groups were assessed by means of analysis of variance.

RESULTS

Intramuscular injection of t-PA, excipient alone, or excipient supplemented with any of the enhancers of absorption without exogenous human t-PA did not elicit immunoradiometrically detectable t-PA in plasma within a 30 to 60 minute interval of observation in any of 31 rabbits or six dogs. Elevation of functional t-PA activity in plasma was not detectable despite sham operation, electrical field stimulation at the injection site, or administration of enhancers of absorption in the absence of administration of exogenous t-PA.

Absorption of intramuscularly injected t-PA with media supplemented with potential enhancers of absorption: Short-term experiments with local electrical stimulation and injections into exposed muscle. Short-term effects in rabbits of hydroxylamine and several potential enhancers of absorption selected from organic amines at a concentration of 0.63M in the injection medium and of hydralazine (0.88 mM), adenosine (7 mM), or hyaluronidase (1000 U/ml) in concentrations chosen to avoid hemodynamic pertubations were evaluated in 120 rabbits. In the absence of an absorption-enhancing agent, the highest plasma t-PA concentration occurred 5 minutes after injection and was barely detectable (8±2 [SD] ng/ml, n=3). Low peaks were seen also with ethylamine (16 ng/ml maximum, n=3) and hyaluronidase (38 ng/ml, n=2). Hydralazine or adenosine independently elevated peak t-PA levels but only trivially (n=3). Histamine (0.65 mg/kg) was ineffective, elevating t-PA to only 18 ng/ml (n=5). Among the remaining agents tested, only diethylamine (88 ng/ml, n=3), methylamine (224±32 ng/ml, n=16), and hydroxylamine (371±44 ng/ml, n=9) elicited marked augmentation of absorption of t-PA. Methylamine 0.63 plus 0.315M hydroxylamine increased plasma t-PA maximally to an average peak of 562±130 ng/ml (n=9) 5 minutes after injection. In each of these experiments four separate injection sites were used because of the modest mass of rabbit muscle. The total amount of t-PA in the entire 4 ml total volume injected was verified by analysis to be consistent (2.5±2.26 mg/kg body weight). Saline in the same concentration as that of hydroxylamine or methylamine (0.63M) augmented absorption of t-PA by less than 30% of that induced by either amine (n=6). The addition of 0.63M NaCl to 0.63M methylamine in the injection medium did not augment absorption of t-PA appreciably beyond that elicited by methylamine alone. With hydroxylamine as the sole enhancer of absorption and the amount of t-PA injected held constant (2.4 mg/kg), peak plasma t-PA occurred within 5 minutes after injection and increased as a function of the total volume of injection from 0.06 ml to 1 ml and 4 ml (in 1 ml aliquots in four sites) from 41±12 to 119±33 and 356±48 ng/ml, respectively (n=13). With the volume of injection media containing 0.63M methylamine held constant (four 1 ml injections in each rabbit), peak plasma t-PA increased monotonically with doses ranging from 2 to 13 mg/kg from an average of 180 to 936 ng/ml occurring within 5 minutes at each dose (averages of results of duplicate experiments at each dose, n=26). Additional experiments (n=22) demonstrated that hydralazine elicited effects comparable to those of electrical stimulation, that the two were not additive, and that each increased peak t-PA compared to that with 0.63M methylamine as the sole enhancer by an average of 96%.

With the exception of hydralazine and adenosine, which elicited modest decreases in arterial pressure and increases in heart rate (both less than 10%), the agent that exerted the most consistent effects on arterial pressure or heart rate monitored over the 30 minute interval after injection was hydroxylamine (Table 1).

TABLE 2

Hemodynamic effects of methylamine and hydroxylamine in rabbits and dogs

| | | Percent of control at selected intervals after injection | | | | | | | |
|---|---|---|---|---|---|---|---|---|---|
| | | Baseline | | 15 min | | 1 hr | | 2 hr | |
| Injector medium | n | HR | MAP | HR | MAP | HR | MAP | HR | MAP |
| Rabbits | | | | | | | | | |
| None (control) | 2 | 275 | 96 | 96 | 91 | | | | |
| 0.63 M methylamine | 8 | 282 | 89 | 88 | 76 | | | | |
| 0.63 M hydroxylamine | 6 | 271 | 91 | 81 | 52[a] | | | | |
| Dogs | | | | | | | | | |
| None (control) | 2 | 82 | 108 | 92 | 99 | 106 | 116 | 97 | 123 |
| 0.63 M methylamine | 2 | 171 | 116 | 101 | 103 | 100 | 84 | 85 | 83 |
| 0.63 M hydroxylamine | 2 | 106 | 104 | 143 | 115 | | | | |
| 0.63 M methylamine plus 0.079 M hydroxylamine | 3 | 78 | 118[b] | 102 | 98 | 91 | 94 | 109 | 108 |

Baseline values are averages of heart rate (HR) and mean arterial blood pressure (MAP). Results after injection are expressed as percentages of control values to normalize for animal-to-animal variation at baseline.

Injections of 1 ml in each of four exposed sites were performed followed by local electrical field stimulation. Hemodynamic changes were more marked in rabbits because of the higher ratio of injection volume and hence the amount of methylamine, hydroxylamine, or both to body weight in rabbits than in dogs. Methemoglobin 1 hr after injection exceeded 11% in dogs given 0.63M hydroxylamine, but was undetectable or less than 0.6% in dogs given 0.63M methylamine alone or 0.63M methylamine plus 0.079M hydroxylamine. It was as high as 48% in rabbits given hydroxylamine (but absent with methylamine) because of the larger ratio of amine given per body weight.

Methoxyamine induced methemoglobinemia, hypoxemia, and hypotension as well. Hydroxylamine elicited an initial 10 to 15 mm Hg decrease in mean arterial pressure with a 30% increase in heart rate immediately after injection. These hemodynamic effects peaked in 2 minutes and abated in approximately 5 minutes. Subsequently, mean arterial pressure declined markedly associated with profound hypoxemia (gross cyanosis) and methemoglobinemia averaging 48%. None of the animals injected with saline, excipient, t-PA and excipient, or t-PA and excipient supplemented with methylamine (0.63M) or with 0.63M methylamine plus 0.079M hydroxylamine, the combination selected as the most promising for enhancement of absorption while devoid of deleterious hemodynamic effects, exhibited significant hemodynamic changes or hypoxemia. Hydroxylamine, methylamine, and all of the other agents did not alter immunoradiometrically detectable t-PA in plasma samples supplemented with human t-PA and incubated for 1 hour at 37° C. whether they were assayed immediately or stored for as long as 1 month at 0° to 4° C.

Histopathologic effects of injections with electrical simulation.

In rabbits. Injection of t-PA in excipient alone ($n=4$) produced only minor skeletal muscle trauma detectable histologically and manifested by localized interstitial hemorrhage and microfocal myonecrosis in a pattern consistent with mechanical trauma per se (i.e., the insertion of the needle and injection of an inert vehicle into the muscle). These changes were indistinguishable from those seen with injection of excipient alone or with isotonic saline ($n=6$).

Hydroxylamine (0.63M in 1.0 ml injected in one site) caused substantial muscle necrosis ($n=27$ animals) readily apparent 48 hours after injection. Injection of this agent elicited discrete zones of skeletal muscle necrosis surrounded by narrow mantles of interstitial hemorrhage. The extent of necrosis was proportional to the volume of the injection but not influenced by the presence or absence of t-PA. Even the most extensive injury seen was confined to the immediate vicinity of the injection site. In contrast, 0.63M methylamine elicited considerably less local injury in volumes of injection ranging from 0.06 to 10 ml/site ($n=23$). In most cases the injury apparent 48 hours after injection was no greater than that seen after injection with t-PA excipient alone. In some sites injected with a 1 ml volume of 0.63M methylamine, modest myonecrosis and interstitial hemorrhage juxtaposed to the needle track were evident.

In dogs. Injection of 0.63M methylamine ($n=8$) or methylamine plus a low concentration of hydroxylamine (0.63M methylamine plus 0.079M hydroxylamine) ($n=8$) in dogs caused only modest morphologic alterations, including interstitial edema, hemorrhage, and acute inflammation. Focal myonecrosis was minimal or absent. The extents of interstitial edema, hemorrhage, and inflammation were related to the volume of injection. In all cases such abnormalities were confined to the immediate vicinity of the injection site. The extent of morphologic abnormality and myonecrosis was no greater in sites injected with methylamine or the combination of methylamine and a low concentration of hydroxylamine than in skeletal muscle injected with excipient alone. Histologic effects after percutaneous injections without electrical stimulation corresponded to those seen with each enhancer of absorption with injections followed by electrical stimulation.

Results of percutaneous intramuscular injections. In aggregate, the results from the first 229 rabbits studied indicated that 0.63M methylamine or 0.63M methylamine plus 0.079M hydroxylamine facilitated absorption of t-PA after direct injection into exposed muscle followed by local electrical stimulation at the injection site without inducing deleterious local effects or physiologic derangements. Accordingly, additional studies were performed in 21 rabbits injected percutaneously without exposure of the muscle and without electrical field stimulation. The amount of t-PA in the injection medium was increased to yield a total dose of 4 mg/kg. Two 1 ml injections were administered to each animal. Peak plasma t-PA levels occurred within 5 minutes and averaged $134 \pm 21$ with 0.63M methylamine plus 0.079M hydroxylamine ($n=8$), the combination of enhancers of absorption found to be most effective. Saline (0.63M) or excipient alone did not elicit substantial elevations within the 30 minute interval of observation after injection. These results confirmed the feasibility of achieving therapeutic blood levels of t-PA promptly after intramuscular injection without the need for electrical stimulation or exposure of the muscle through skin incisions. They indicated that peak blood levels could be obtained within 5 minutes after injection with the specific enhancers of absorption of the present invention that increase vascular permeability.

Absorption of t-PA injected intramuscularly and its functional consequences in dogs. Effective coronary thrombolysis with t-PA requires early and sustained elevation of t-PA in plasma. To determine whether both could be accomplished and to assess the functional impact of intramuscular t-PA on the fibrinolytic system and on coronary thrombin, additional experiments were performed in dogs.

Initial results indicated that intramuscular administration of large amounts of t-PA (10 mg/kg) in two simultaneous injections of 2 ml each in the absence of enhancers of absorption did not elevate plasma t-PA values early after injection. Thus values 15 minutes after injection averaged only 44 ng/ml ($n=2$) despite the large amount of t-PA administered. Sustained elevations 90 minutes or more after injections averaging $339 \pm 42$ and $622 \pm 86$ (SD) ng/ml were seen, however, in each of the two dogs ($n=10$ observations per dog). These persisted for the entire 6 hour interval of observation. Considering results from the 250 rabbits studied and these two dogs, it appeared likely to us that the response of t-PA given intramuscularly was biphasic. Early absorption appeared to be dependent on the presence of the enhancer of absorption. Later plasma elevations appeared to reflect the slow ingress of t-PA in the circulation relatively independent of the presence or absence of an enhancer. This was confirmed by experiments performed in dogs given 10 mg/kg t-PA intramuscularly with excipient alone, 0.63M methylamine, or 0.63M methylamine plus 0.079M hydroxylamine. Elevations of t-PA within 20 minutes were trivial without enhancer, averaging only 32 ng/ml (n=3); modest with 0.63M methylamine, averaging 126 ng/ml (n=3); and marked with 0.63M methylamine plus 0.079M hydroxylamine, averaging 297 ng/ml (n=3). Intramuscular injection of t-PA with 0.63M methylamine plus 0.079M hydroxylamine resulted in both an early, enhancer-dependent peak and sustained elevations persisting for the entire 6 hours of observation, whereas with excipient alone only the late elevations were apparent. The elevations of plasma t-PA antigen were accompanied by elevation of functional activity generally consistent with the measured ratio of functional-to-antigenic activity of the t-PA injected. Thus the ratio of functional activity to t-PA antigen in plasma after intramuscular injection of t-PA with methylamine and hydroxylamine averaged 0.31±0.02 (SD) IU/ng (n=44 samples obtained over 6 hours after injection from three dogs). The magnitude and persistence of elevations of plasma t-PA are consistent with bioavailability of approximately 50% of injected t-PA in the 6 hour interval studied. Circulating fibrinogen did not decline detectably, although $\alpha_2$-antiplasmin decreased by 70% over 6 hours reflecting persistent elevation of functional t-PA activity.

While with no enhancer the t-PA in the blood in the dogs was only 44 ng/ml after 15 minutes and required over 2 hours and 40 minutes to reach 240 ng/ml, with the use of the enhancer (0.079M) hydroxylamine hydrochloride together with 0.63M methylamine hydrochloride, the t-PA level in the dog tested was about 200 ng/ml within 5 minutes and reached about 300 ng/ml within 15 minutes.

Effects on coronary thrombolysis. As indicated in the section Materials and Methods, coronary thrombin were induced in dogs with percutaneously inserted, indwelling coronary arterial copper coils. The coils are markedly thrombogenic and consistently induce persistent coronary thrombosis within 2±1 (SD) minutes (n=17 control dogs given no t-PA). Full heparinization fails to lead to recanalization of the occluded coronary artery.

To determine whether 10 mg/kg t-PA administered intramuscularly with 0.63M methylamine plus 0.079M hydroxylamine elicited coronary thrombolytic effects rapidly with biological activity persisting over prolonged intervals, two dogs with coronary thrombosis induced with copper coils were studied. Occlusive clots were confirmed angiographically, and thrombolysis was initiated with two simultaneous, percutaneous intramuscular injections of 2 ml each of t-PA (10 mg/kg total dose) in 0.63M methylamine hydrochloride plus 0.079M hydroxylamine hydrochloride 7 to 10 minutes after documented thrombosis. In both dogs, clot lysis occurred within 60 minutes despite the persistent presence of the intracoronary thrombogenic copper coils. Furthermore, coronary thrombolytic effects were evident throughout a 6 hour interval of observation after a single intramuscular administration of t-PA even though no heparin was given, manifested by repetitive recanalization after the anticipated, episodic reocclusion induced by the indwelling, thrombogenic copper coil. These results indicate that (1) substantial elevations of plasma t-PA can be obtained within minutes after intramuscular injection when enhancers of absorption are employed; and (2) thrombolytic effects are persistent for at least 6 hours after injection.

In summary it has been found:

(1) Intramuscularly administered t-PA is absorbed slowly in the absence of enhancers of absorption, with plasma levels rising substantially only slowly but persisting for at least 6 hours.

(2) Inclusion of hydroxylamine or a salt thereof in injection medium results in prompt absorption of t-PA with marked elevation of plasma t-PA occurring within 5 minutes after injection.

(3) Concentrations of hydroxylamine required to enhance early absorption optimally result in local injury, methemoglobinemia, and hemodynamic derangements especially marked in rabbits compared with dogs because of the greater amount of agent given per kilogram of body weight.

(4) Prompt absorption of t-PA is facilitated by methylamine or a salt thereof, agents that do not exhibit deleterious local efforts or systemic derangements seen with high concentrations of hydroxylamine.

(5) The combination of methylamine or a salt thereof with a low concentration of hydroxylamine or a salt thereof augments initial absorption beyond that seen with methylamine or a salt thereof alone without deleterious local or systemic effects.

(6) Substantial initial absorption of t-PA is elicited with percutaneous intramuscular injections in intact rabbits and dogs without local electrical stimulation.

(7) t-PA absorbed after intramuscular injection with the enhancers identified is functionally active throughout 6 hours of observation in dogs, judging from functional assay of t-PA activity in plasma, consumption of $\alpha_2$antiplasmin in vivo, and sequential coronary angiograms demonstrating repetitive clot lysis even when a thrombogenic intracoronary copper coil remains in place and no heparin is given.

In all of the experimental work described in this application both the hydroxylamine and the methylamine were employed as the hydrochloride salt.

The compositions can comprise, consist essentially of or consist of the recited materials.

EXAMPLE 1

In following Table 2 the procedure employed was to inject the rabbits intramuscularly substantially simultaneously with solutions from 2 vials, each vial containing 1 ml of solution. Each vial contained 2 mg/kg of body weight of t-PA (i.e. each rabbit received a total of 4 mg/kg body weight) and each vial given to rabbits 1, 2 and 3 was 0.63 molar in methylamine hydrochloride and 0.079 molar in hydroxylamine hydrochloride. The solutions were buffered to pH 7.2 with arginine phosphate.

In the table MA is the abbreviation for methylamine hydrochloride and HA is the abbreviation for hydroxylamine hydrochloride.

The abbreviations ELISA stands for Enzyme Linked Immunosorbent Assay and is the method employed for analysis for the t-PA remaining in the blood at the indicated time in minutes, the amount of t-PA being expressed in nanograms per milliliter.

TABLE 2

|  | Rabbit 1 | Rabbit 2 | Rabbit 3 |
|---|---|---|---|
| Solution Content |  |  |  |
| 0.63 M MA | Yes | Yes | Yes |
| 0.079 M HA | Yes | Yes | Yes |
| Mls Injected | 2 × 1 ml | 2 × 1 ml | 2 × 1 ml |
| rt-PA (4 mg/kg) | 9.6 mg | 9.2 mg | 8.8 mg |

TABLE 2-continued

| Time (minutes) | Rabbit 1 | Rabbit 2 | Rabbit 3 |
|---|---|---|---|
| ELISA Results ng/ml t-PA | | | |
| 5 | 71 | 147 | 73 |
| 10 | 55 | 81 | 66 |
| 15 | 52 | 70 | 44 |
| 30 | 57 | 67 | 32 |

While the invention is primarily directed to enhancing the absorption of intramuscularly injected t-PA, it is also considered to be useful in enhancing the absorption of other clot selective protein thrombolytic agents, as mentioned in the Sarnoff patents and applications referred to above.

EXAMPLE 2

In viewing Table 3, the procedure employed was to inject each dog intramuscularly substantially simultaneously with a solution containing t-PA and enhancer(s). Each dog received a total injected volume of 4 ml containing 10 mg/kg t-PA body weight. The solution was administered in two separate sites (i.e., 2 ml per site). The enhancer combination employed was either 0.63M methylamine hydrochloride or 0.63M methylamine hydrochloride and 0.079M hydroxylamine hydrochloride. The solutions were buffed to pH 7.2 with arginine phosphate.

In the Table, MA is the abbreviation for methylamine hydrochloride and HA is the abbreviation for hydroxylamine hydrochloride.

The abbreviation ELISA stands for Enzyme Linked Immunosorbent Assay and is the method employed for analysis for the t-PA remaining in the blood at the indicated time in minutes, the amount of t-PA being expressed in nanograms per milliliter.

TABLE 3

| Solution Content | Dog 1 | Dog 2 |
|---|---|---|
| 0.63 M MA | X | |
| 0.63 M MA + 0.79 M HA | | X |
| mls injected | 2 × 2 ml | 2 × 2 ml |
| mg/ml t-PA assayed | 50 mg/ml | 48 m/ml |
| ELISA results (ng/ml t-PA) | | |
| Time (minutes) | | |
| 5 | 56 | 179 |
| 10 | 14 | 292 |
| 15 | 74 | 284 |
| 30 | 114 | 200 |

The term t-PA or tissue-type plasminogen activator as used in the claims is used in its functional sense and includes not only natural t-PA but modifications and derivatives of t-PA that convert plasminogen to plasmin mainly at the clot rather than in the systemic circulation. The modifications and derivatives included may also have more prolonged activity and/or require less absorption enhancer and/or be more clot selective and/or be more rapidly effective than natural t-PA.

It thus will be seen that the objects of this invention have been fully and effectively accomplished. It will be realized, however, that the foregoing preferred specific embodiment has been shown and described for the purpose of illustrating the functional and structural principles of this invention and is subject to change without departure from such principles. Therefore, this invention includes all modifications encompassed within the spirit and scope of the following claims.

We claim:

1. A method comprising intramuscularly administering t-PA to a mammal in need thereof and increasing the absorption of the t-PA in the blood comprising substantially at the same time intramuscularly administering (1) methylamine or a non-toxic salt thereof and (2) hydroxylamine or a non-toxic salt thereof, the hydroxylamine or non-toxic salt thereof being administered in an amount sufficient to increase the absorption of the t-PA and the methylamine or non-toxic salt thereof being administered in an amount sufficient to reduce the amount of hydroxylamine or non-toxic salt thereof required to give the increased absorption of t-PA.

2. A method according to claim 1 wherein there is employed a non-toxic salt of methylamine and a non-toxic salt of hydroxylamine.

3. A method according to claim 2 wherein there are employed methylamine hydrochloride and hydroxylamine hydrochloride.

4. A package containing (1) t-PA, (2) methylamine or a non-toxic salt thereof and (3) hydroxylamine or a non-toxic salt thereof, the amount of hydroxylamine or non-toxic salt thereof being sufficient to increase the absorption in the blood of the t-PA when it is administered non-intravascularly to a mammal and the amount of methylamine or non-toxic salt thereof being sufficient to reduce the amount of hydroxylamine or non-toxic salt thereof required to obtain the increased absorption of t-PA.

5. A package according to claim 4 wherein there is employed a non-toxic salt of methylamine and a non-toxic salt of hydroxylamine.

6. A package according to claim 5 wherein there is employed methylamine hydrochloride and hydroxylamine hydrochloride.

7. A package containing an aqueous solution having a concentration of 0.02 to 0.79 moles per liter of hydroxylamine or a non-toxic salt thereof and an aqueous solution having a concentration of 0.02 to 6.3 moles per liter of methylamine or a non-toxic salt thereof.

8. A package according to claim 7 wherein the hydroxylamine or salt thereof and the methylamine or salt thereof are together in a single solution.

9. A package according to claim 7 wherein the solution of hydroxylamine or salt thereof is in a first container in the package and the solution of methylamine or salt thereof is in a second container in the package.

10. A package according to claim 7 wherein there is employed an aqueous solution of a hydroxylamine salt and an aqueous solution of a methylamine salt.

11. A package according to claim 10 where there are present hydroxylamine hydrochloride and methylamine hydrochloride.

12. A package according to claim 11 including t-PA.

13. A package according to claim 7 including t-PA.

14. A method comprising intramuscularly administering a clot selective protein thrombolytic agent to a mammal in need thereof and increasing the absorption of the clot selective protein thrombolytic agent in the blood comprising substantially at the same time intramuscularly administering (1) methylamine or a non-toxic salt thereof and (2) hydroxylamine or a non-toxic salt thereof, the hydroxylamine or non-toxic salt thereof being administered in an amount sufficient to increase the absorption of the clot selective protein thrombolytic agent and the methylamine or non-toxic salt thereof being administered in an amount sufficient to reduce the amount of hydroxylamine or non-toxic salt thereof required to give the increased absorption of the protein thrombolytic agent.

15. A method according to claim 14 wherein there is employed a non-toxic salt of methylamine and a non-toxic salt of hydroxylamine.

16. A method according to claim 15 wherein there are employed methylamine hydrochloride and hydroxylamine hydrochloride.

* * * * *